US009746359B2

(12) United States Patent
Desilva et al.

(10) Patent No.: US 9,746,359 B2
(45) Date of Patent: Aug. 29, 2017

(54) FLOW SENSOR

(71) Applicant: Vyaire Medical Capital LLC, Yorba Linda, CA (US)

(72) Inventors: Adrian D. Desilva, Riverside, CA (US); Huy Thanh Vu, Westminster, CA (US); Richard Le, Oceanside, CA (US); Jeffrey Harold Miller, Irvine, CA (US); Hector Gonzalez, Corona, CA (US); Raul Valdez, Eastvale, CA (US); Chiun Wang, Cypress, CA (US)

(73) Assignee: VYAIRE MEDICAL CAPITAL LLC, Yorba Linda, CA (US)

( * ) Notice: Subject to any disclaimer, the term of this patent is extended or adjusted under 35 U.S.C. 154(b) by 264 days.

(21) Appl. No.: 13/931,486

(22) Filed: Jun. 28, 2013

(65) Prior Publication Data
US 2015/0000655 A1    Jan. 1, 2015

(51) Int. Cl.
*G01F 1/50* (2006.01)
*A61M 16/00* (2006.01)
(Continued)

(52) U.S. Cl.
CPC ............ *G01F 1/50* (2013.01); *A61M 16/0051* (2013.01); *A61M 16/12* (2013.01); *G01F 1/36* (2013.01);
(Continued)

(58) Field of Classification Search
None
See application file for complete search history.

(56) References Cited

U.S. PATENT DOCUMENTS

| 2,037,880 A | 4/1936 | Charavay |
| 2,510,125 A | 6/1950 | Meakin |

(Continued)

FOREIGN PATENT DOCUMENTS

| CN | 1041204 A | 4/1990 |
| CN | 101225881 A | 7/2008 |

(Continued)

OTHER PUBLICATIONS

International Search Report and Written Opinion for International Application No. PCT/US2014/044737, dated May 19, 2015, 18 pages.

(Continued)

*Primary Examiner* — (Jackie) Tan-Uyen T Ho
*Assistant Examiner* — Joseph D Boecker
(74) *Attorney, Agent, or Firm* — McDermott Will & Emery LLP

(57) ABSTRACT

A flow sensor comprises a flow restriction disposed within a passage such that a fluid passing through the passage must pass through the flow restriction. The flow sensor also has an upstream pressure sensor coupled to the passage at a point upstream of the flow restriction and configured to measure and provide an upstream pressure of the fluid within the passage, a downstream pressure sensor coupled to the passage at a point downstream of the flow restriction and configured to measure and provide a downstream pressure of the fluid within the passage, and a temperature sensor coupled to the passage and configured to measure and provide a temperature of the fluid within the passage. The flow sensor also includes a flow sensor processor coupled to the upstream and downstream pressure sensors and the temperature sensor and configured to accept measurements therefrom and calculate a compensated flow rate based at least in part on the measured pressures and temperature.

20 Claims, 5 Drawing Sheets

(51) Int. Cl.
*A61M 16/10* (2006.01)
*A61M 16/12* (2006.01)
*G01F 1/36* (2006.01)
*A61M 16/16* (2006.01)

(52) U.S. Cl.
CPC ..... *A61M 16/0066* (2013.01); *A61M 16/1045* (2013.01); *A61M 16/16* (2013.01); *A61M 2016/0027* (2013.01); *A61M 2016/0039* (2013.01); *A61M 2202/025* (2013.01); *A61M 2202/0208* (2013.01); *A61M 2205/3368* (2013.01); *A61M 2205/3569* (2013.01); *A61M 2205/3592* (2013.01); *A61M 2205/505* (2013.01)

(56) References Cited

U.S. PATENT DOCUMENTS

| | | | |
|---|---|---|---|
| 2,634,311 A | 4/1953 | Darling | |
| 3,140,042 A | 7/1964 | Fujii | |
| 3,673,541 A | 6/1972 | Volinskie | |
| 3,776,215 A | 12/1973 | Howard et al. | |
| 3,788,765 A | 1/1974 | Rusak | |
| 4,167,369 A | 9/1979 | Ishihara | |
| 4,243,357 A | 1/1981 | Flynn et al. | |
| 4,381,668 A | 5/1983 | Sato et al. | |
| 4,406,161 A * | 9/1983 | Locke | G01F 1/88 73/114.33 |
| 4,543,041 A | 9/1985 | French et al. | |
| 4,562,744 A * | 1/1986 | Hall | G01F 1/88 73/861.02 |
| 4,571,801 A | 2/1986 | Ewing | |
| 4,602,653 A * | 7/1986 | Ruiz-Vela | A61M 16/12 128/204.22 |
| 4,649,760 A | 3/1987 | Wedding | |
| 4,754,651 A | 7/1988 | Shortridge et al. | |
| 4,763,645 A | 8/1988 | Kapp | |
| 4,809,742 A | 3/1989 | Grau | |
| 4,825,904 A | 5/1989 | Grau et al. | |
| 4,909,545 A | 3/1990 | Hohol | |
| 4,978,281 A | 12/1990 | Conger, IV | |
| 5,064,346 A | 11/1991 | Atarashi et al. | |
| 5,127,400 A | 7/1992 | DeVries et al. | |
| 5,190,068 A * | 3/1993 | Philbin | G01F 15/024 137/486 |
| 5,265,594 A | 11/1993 | Olsson et al. | |
| 5,277,196 A | 1/1994 | Hankinson et al. | |
| 5,295,397 A * | 3/1994 | Hall | G01F 1/363 137/44 |
| 5,331,995 A | 7/1994 | Westfall et al. | |
| 5,339,807 A | 8/1994 | Carter | |
| 5,365,795 A * | 11/1994 | Brower, Jr. | G01F 1/363 73/861.63 |
| 5,461,932 A * | 10/1995 | Hall | G01F 1/42 138/40 |
| 5,478,206 A | 12/1995 | Prahst | |
| 5,537,992 A * | 7/1996 | Bjoernstijerna | A61M 16/1015 128/200.19 |
| 5,572,992 A * | 11/1996 | Kankkunen | A61M 16/186 128/202.27 |
| 5,604,681 A | 2/1997 | Koeninger | |
| 5,606,236 A | 2/1997 | Tennies et al. | |
| 5,676,132 A * | 10/1997 | Tillotson | A61B 5/0878 128/204.23 |
| 5,771,884 A | 6/1998 | Yarnall et al. | |
| 5,918,596 A * | 7/1999 | Heinonen | A61M 16/12 128/204.21 |
| 5,954,051 A | 9/1999 | Heinonen et al. | |
| 6,017,315 A | 1/2000 | Starr et al. | |
| 6,139,262 A | 10/2000 | Ravidranath | |
| 6,151,557 A | 11/2000 | Broden et al. | |
| 6,422,092 B1 * | 7/2002 | Morrison | G01F 1/50 73/861.04 |
| 6,422,256 B1 * | 7/2002 | Balazy | G05D 7/0635 137/12 |
| 6,553,923 B2 | 4/2003 | Gatley, Jr. | |
| 6,578,818 B1 | 6/2003 | Krimmer et al. | |
| 6,609,431 B1 | 8/2003 | Tietsworth et al. | |
| 6,622,724 B1 | 9/2003 | Truitt et al. | |
| 6,769,463 B2 * | 8/2004 | Vu | F16K 27/003 137/486 |
| 6,820,620 B2 | 11/2004 | Rochat | |
| 6,945,123 B1 * | 9/2005 | Kuehl | A61M 16/01 73/861.42 |
| 7,107,834 B2 | 9/2006 | Meneghini et al. | |
| 7,121,139 B2 * | 10/2006 | Shajii | G01F 5/00 73/202.5 |
| 7,636,640 B2 | 12/2009 | Wang et al. | |
| 7,819,022 B2 | 10/2010 | Hope | |
| 7,826,986 B2 | 11/2010 | McDonald | |
| 8,504,318 B2 | 8/2013 | Mendelson et al. | |
| 9,003,877 B2 | 4/2015 | Qasimi et al. | |
| 2002/0085952 A1 | 7/2002 | Ellingboe et al. | |
| 2002/0198668 A1 | 12/2002 | Lull et al. | |
| 2003/0106554 A1 | 6/2003 | de Silva et al. | |
| 2003/0220605 A1 | 11/2003 | Bowman et al. | |
| 2004/0000353 A1 * | 1/2004 | Jones | B64D 13/08 141/64 |
| 2004/0074311 A1 * | 4/2004 | Lull | G01F 1/696 73/861 |
| 2004/0177703 A1 * | 9/2004 | Schumacher | G01F 1/363 73/861.52 |
| 2004/0187871 A1 | 9/2004 | Kimmel et al. | |
| 2005/0004534 A1 | 1/2005 | Lockwood et al. | |
| 2005/0241412 A1 | 11/2005 | Tison et al. | |
| 2006/0079765 A1 | 4/2006 | Neer et al. | |
| 2006/0144163 A1 | 7/2006 | Friberg | |
| 2006/0162466 A1 | 7/2006 | Wargo et al. | |
| 2006/0236781 A1 | 10/2006 | Ohmi et al. | |
| 2007/0193369 A1 | 8/2007 | Evans et al. | |
| 2007/0265877 A1 | 11/2007 | Rice et al. | |
| 2007/0277824 A1 | 12/2007 | Aylsworth et al. | |
| 2008/0059084 A1 | 3/2008 | Wang et al. | |
| 2008/0092891 A1 | 4/2008 | Cewers | |
| 2008/0105259 A1 | 5/2008 | de Silva et al. | |
| 2008/0283062 A1 * | 11/2008 | Esposito, Jr. | A61B 5/061 128/204.23 |
| 2009/0038615 A1 | 2/2009 | Bradley | |
| 2009/0093774 A1 * | 4/2009 | Wang | A61M 5/142 604/247 |
| 2009/0095068 A1 | 4/2009 | Redemann et al. | |
| 2009/0113996 A1 | 5/2009 | Wang et al. | |
| 2009/0293634 A1 | 12/2009 | Ong | |
| 2009/0326839 A1 | 12/2009 | Rogers et al. | |
| 2010/0031737 A1 * | 2/2010 | Saito | G01F 5/00 73/114.33 |
| 2010/0139660 A1 | 6/2010 | Adahan | |
| 2010/0229967 A1 | 9/2010 | Yasuda et al. | |
| 2010/0236552 A1 | 9/2010 | Kwok et al. | |
| 2010/0307490 A1 | 12/2010 | Broborg et al. | |
| 2011/0100364 A1 | 5/2011 | Faram | |
| 2011/0126834 A1 | 6/2011 | Winter et al. | |
| 2011/0126837 A1 | 6/2011 | Winter et al. | |
| 2011/0301867 A1 * | 12/2011 | Davis | G01F 1/88 702/30 |
| 2012/0065533 A1 | 3/2012 | Carrillo, Jr. et al. | |
| 2012/0085349 A1 | 4/2012 | Tobias et al. | |
| 2012/0185102 A1 | 7/2012 | Skoglund et al. | |
| 2012/0204874 A1 | 8/2012 | Sofranko | |
| 2012/0226449 A1 * | 9/2012 | Delache | G01F 1/36 702/45 |
| 2012/0229272 A1 | 9/2012 | Jacob et al. | |
| 2012/0285454 A1 | 11/2012 | Nibu et al. | |
| 2012/0285455 A1 | 11/2012 | Varga et al. | |
| 2012/0318383 A1 * | 12/2012 | Yasuda | G05D 7/0635 137/455 |
| 2013/0036806 A1 * | 2/2013 | Kohno | G01F 1/684 73/114.33 |
| 2013/0079667 A1 | 3/2013 | Berkcan et al. | |
| 2013/0153040 A1 * | 6/2013 | Goto | G01F 1/6847 137/8 |

(56) References Cited

U.S. PATENT DOCUMENTS

| | | |
|---|---|---|
| 2013/0220314 A1 | 8/2013 | Bottom |
| 2013/0247905 A1 | 9/2013 | Miller et al. |
| 2014/0054479 A1 | 2/2014 | Shen |
| 2014/0066880 A1* | 3/2014 | Prince ............... A61M 5/16881 604/500 |
| 2014/0182590 A1 | 7/2014 | Platt et al. |
| 2014/0195172 A1* | 7/2014 | Le ........................ G01F 5/005 702/47 |
| 2014/0251322 A1 | 9/2014 | Miller |
| 2015/0020807 A1 | 1/2015 | Kimmel |
| 2015/0096560 A1 | 4/2015 | Klenner et al. |
| 2015/0143921 A1 | 5/2015 | Postberg et al. |
| 2016/0256646 A1 | 9/2016 | Vazales |

FOREIGN PATENT DOCUMENTS

| | | |
|---|---|---|
| CN | 101687086 A | 3/2010 |
| CN | 102155570 A | 8/2011 |
| CN | 202366282 U | 8/2012 |
| CN | 102686888 A | 9/2012 |
| CN | 102927292 A | 2/2013 |
| CN | 103041492 A | 4/2013 |
| CN | 202870631 U | 4/2013 |
| EP | 0829793 A1 | 3/1998 |
| EP | 1127583 A2 | 8/2001 |
| EP | 1658874 A2 | 5/2006 |
| EP | 2402616 A1 | 1/2012 |
| JP | S56597 A | 1/1981 |
| WO | WO-0138832 A2 | 5/2001 |
| WO | WO-2006024532 A1 | 3/2006 |
| WO | WO-2011055254 A1 | 5/2011 |
| WO | WO-2013002699 A1 | 1/2013 |

OTHER PUBLICATIONS

Invitation to Pay Additional Fees in International Application No. PCT/US2014/044737 dated Oct. 28, 2014, 7 pages.
International Search Report for International Application No. PCT/US2014/044743, dated Jan. 22, 2015, 6 pages.
International Search Report and Written Opinion in PCT Application No. PCT/US2014/044438 dated Oct. 28, 2014, 11 pages.
International Search Report and Written Opinion in PCT Application No. PCT/US2014/044441 dated Oct. 31, 2014, 12 pages.
International Search Report and Written Opinion in PCT Application No. PCT/US2014/044724 dated Oct. 21, 2014, 12 pages.
Invitation to Pay Additional Fees in PCT Application No. PCT/US2014/044743 dated Oct. 21, 2014, 7 pages.
International Search Report and Written Opinion in PCT Application No. PCT/US2014/044442 dated Nov. 3, 2014, 10 pages.
International Search Report and Written Opinion for Application No. PCT/US2015/038157, dated Nov. 5, 2015, 12 pages.
Invitation to Pay Additional Fees and Partial Search Report for Application No. PCT/US2015/038155, dated Oct. 7, 2015, 7 pages.
International Search Report and Written Opinion for Application No. PCT/US2015/038155, dated Dec. 17, 2015, 18 pages.
Chinese Office Action for Application No. 201480036606.9, dated Sep. 2, 2016, 6 pages excluding translation.
Chinese Office Action for Application No. 201480036971.X, dated Oct. 8, 2016, 10 pages excluding English translation.
Chinese Office Action for Application No. 201480037104.8, dated Nov. 17, 2016, 5 pages excluding English translation.
Chinese Office Action for Application No. 201480037090.X, dated Sep. 26, 2016, 6 pages excluding English translation.

* cited by examiner

FLOW SENSOR

CROSS-REFERENCES TO RELATED APPLICATIONS

This application is related to co-pending U.S. application Ser. No. 13/931,566, filed Jun. 28, 2013, entitled "MODULAR FLOW CASSETTE," U.S. application Ser. No. 13/931,418, filed Jun. 28, 2013, U.S. Pat. No. 9,433,743, entitled "VENTILATOR EXHALATION FLOW VALVE," and U.S. application Ser. No. 13/931,496, filed Jun. 28, 2013, entitled "FLUID INLET ADAPTER".

BACKGROUND

Field

The present disclosure generally relates to measurement of gas flow rates and, in particular, to accurate measurement of the flow rate of multiple gases.

Description of the Related Art

Patients with respiratory injury, such as chronic respiratory failure, may be provided with a respirator to assist with their breathing or, in severe cases, take over the breathing function entirely. Respirators typically provide a flow of air, or other breathing gases, at an elevated pressure during an inhalation interval, followed by an exhalation interval where the pressurized air is diverted so that the air within the patient's lungs can be naturally expelled.

Conventional respirators may be configured to accept one or more breathing gases, for example "pure oxygen" or "heliox 80/20" (a mixture of 80% helium with 20% oxygen) from external sources. The exact gas mixture delivered to the patient, however, may be a mixture of various breathing gases since the specific percentage required for a particular patient may not be commercially available and must be custom mixed in the respirator.

It is important to provide precisely the specified flow rate of gas to the patient, particularly for neonatal patients whose lungs are small and very susceptible to damage from over-inflation.

SUMMARY

It is advantageous to provide an accurate flow measurement of a variety of gases and gas mixtures over a range of temperatures and flow rates.

In certain embodiments, a flow sensor is disclosed that comprises a flow restriction disposed within a passage such that a fluid passing through the passage must pass through the flow restriction, an upstream pressure sensor coupled to the passage at a point upstream of the flow restriction and configured to measure and provide an upstream pressure of the fluid within the passage, a downstream pressure sensor coupled to the passage at a point downstream of the flow restriction and configured to measure and provide a downstream pressure of the fluid within the passage, a temperature sensor coupled to the passage and configured to measure and provide a temperature of the fluid within the passage, and a flow sensor processor coupled to the upstream and downstream pressure sensors and the temperature sensor and configured to accept measurements therefrom and calculate a compensated flow rate based at least in part on the measured pressures and temperature.

In certain embodiments, a method is disclosed that includes the steps of identifying a fluid passing through a flow restriction, measuring a pressure drop across the flow restriction, retrieving compensation parameters that comprise information associated with characteristics of the identified fluid flowing through the flow restriction, and calculating with a processor a compensated flow rate.

In certain embodiments, a ventilator is disclosed that includes an output flow channel configured to mate with a supply limb, an input flow channel configured to accept a gas from a source, and a flow sensor that has a flow restriction disposed within a passage coupled between the input flow channel and the output flow channel such that the gas passing through the passage must pass through the flow restriction, an upstream pressure sensor coupled to the passage at a point upstream of the flow restriction and configured to measure and provide an upstream pressure of the gas within the passage, a downstream pressure sensor coupled to the passage at a point downstream of the flow restriction and configured to measure and provide an downstream pressure of the gas within the passage. The flow sensor also has a temperature sensor coupled to the passage and configured to measure and provide a temperature of the gas within the passage and a flow sensor processor coupled to the upstream and downstream pressure sensors and the temperature sensor and configured to accept measurements therefrom and calculate a compensated flow rate based at least in part on the measured pressures and temperature.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
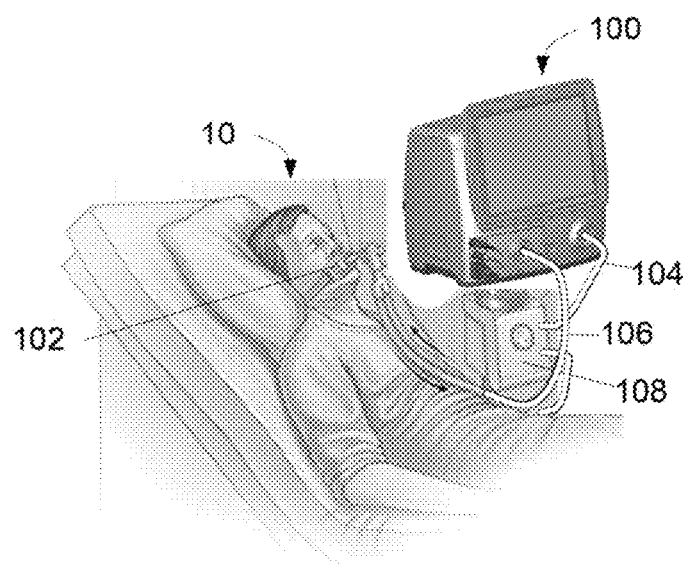
FIG. 1 depicts a patient using an exemplary ventilator according to certain aspects of the present disclosure.

It is advantageous to provide an accurate flow measurement of a variety of gases and gas mixtures over a range of temperatures and flow rates.

The disclosed systems and methods of measuring flow rates and compensating for the composition of the gas or gas mixture as well as the temperature of the measured gas provides increased accuracy compared to flow measurements made within conventional ventilators.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

While the discussion herein is directed to a ventilator for use in a hospital, the disclosed concepts and methods may be applied to environments, such as a home or long-term care facility, and other fields, such as deep-sea diving, that would benefit from accurate flow measurement of a variety of gas mixtures. Those of skill in the art will recognize that these same features and aspects may also be applied to the sensing of flow rates of other fluids besides medical gases.

Within this document, the term "gas" shall be interpreted to mean both a single material in gaseous form, for example oxygen, and a mixture of two or more gases, for example air or heliox. A gas may include water or other liquids in the form of vapor or suspended droplets. A gas may also include solid particulates suspended in the gas.

Within this document, the term "pure," when used with reference to a gas, means that the gas meets commonly accepted medical standards for purity and content.

Within this document, the term "heliox" means a mixture of pure oxygen and pure helium. The mixture may contain a designated percentage of each gas, for example "heliox 70/30" containing approximately 70% helium and 30% oxygen. Heliox may contain trace amounts of other gases.

Within this document, the term "temperature sensor" means a device configured to measure temperature and provide a signal that is related to the measured temperature. A temperature sensor may include electronics to provide a drive current or voltage and/or measure a current or voltage. The electronics may further include conditioning and conversion circuitry and/or a processor to convert the measured value to a signal that may be in analog or digital form.

Within this document, the term "pressure sensor" means a device configured to measure a gas pressure and provide a signal that is related to the measured pressure. A pressure sensor may include electronics to provide a drive current or voltage and/or measure a current or voltage. The electronics may further include conditioning and conversion circuitry and/or a processor to convert the measured value to a signal that may be in analog or digital form. The pressure may be provided in absolute terms or "gauge" pressure, i.e. relative to ambient atmospheric pressure.

Within this document, the term "Hall effect sensor" means a device configured to detect the presence of a magnet or other magnetic element without making physical contact (non-contacting). A temperature sensor may include electronics to provide a drive current or voltage and/or measure a current or voltage. The electronics may further include conditioning and conversion circuitry and/or a processor to convert the measured value to a signal that may be in analog or digital form.

FIG. 1 depicts a patient 10 using an exemplary ventilator 100 according to certain aspects of the present disclosure. In this example, the ventilator 100 is connected to the patient 10 a supply tube or "limb" 104 and a return or exhaust limb 106. There may be a conditioning module 108 coupled to the supply limb 104 that may, for example, warm or humidify the air passing through the supply limb 104. The supply and exhaust limbs 104, 106 are both coupled to a patient interface device 102 that, in this example, is a mask that fits over the mouth of the patient 10. In other embodiments (not shown in FIG. 1), the patient interface device 102 may include a nasal mask, an intubation device, or any other breathing interface device as known to those of skill in the art.

Figure 2A:
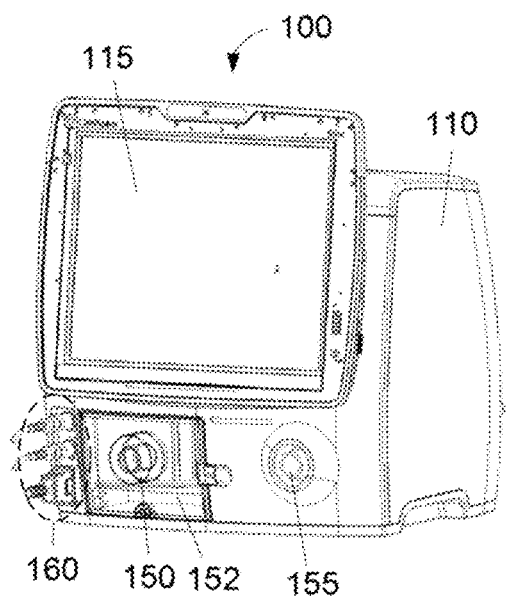
FIGS. 2A and 2B are front and rear views of an exemplary ventilator according to certain aspects of the present disclosure.
Figure 2B:
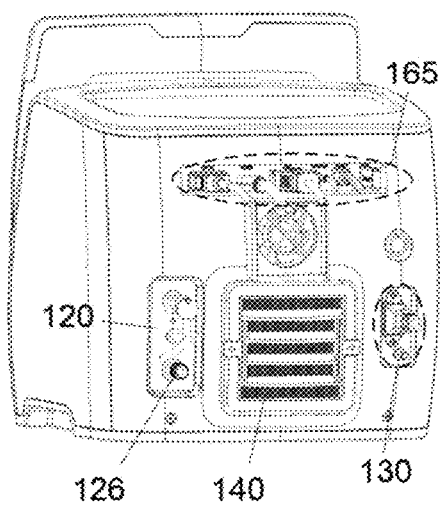

FIGS. 2A and 2B are front and rear views of the ventilator 100 according to certain aspects of the present disclosure. The ventilator 100 has a housing 110 with an attached user interface 115 that, in certain embodiments, comprises a display and a touchscreen. In FIG. 2A, it can be seen that the front of the housing 110 includes a supply port 155 for a supply limb, such as supply limb 104 in FIG. 1, and a return port 150 for a exhaust limb, such as exhaust limb 106 in FIG. 1. The return port 150 may be mounted over an access door 152 that provides access to a filter (not visible in FIG. 2A) that filters and absorbs moisture from the exhaled breath of the patient 10. In certain embodiments, there may also be a front connection panel 160 for connection to, for example, external instruments, sensors, or sensor modules. FIG. 2B shows a rear view of the ventilator 100 with a gas inlet adapter 120, an air intake port 140, and a power interface 130 that may include a power plug connector and a circuit breaker reset switch. There may also be a rear interface panel 165 for connection to external instruments or a network interface cable. A flow cassette 200 is installed within the housing 110 behind the gas inlet adapter 120 and in fluid communication between the inlet connector 126 shown in FIG. 2B and the supply port 155 shown in FIG. 2A.

Figure 3:
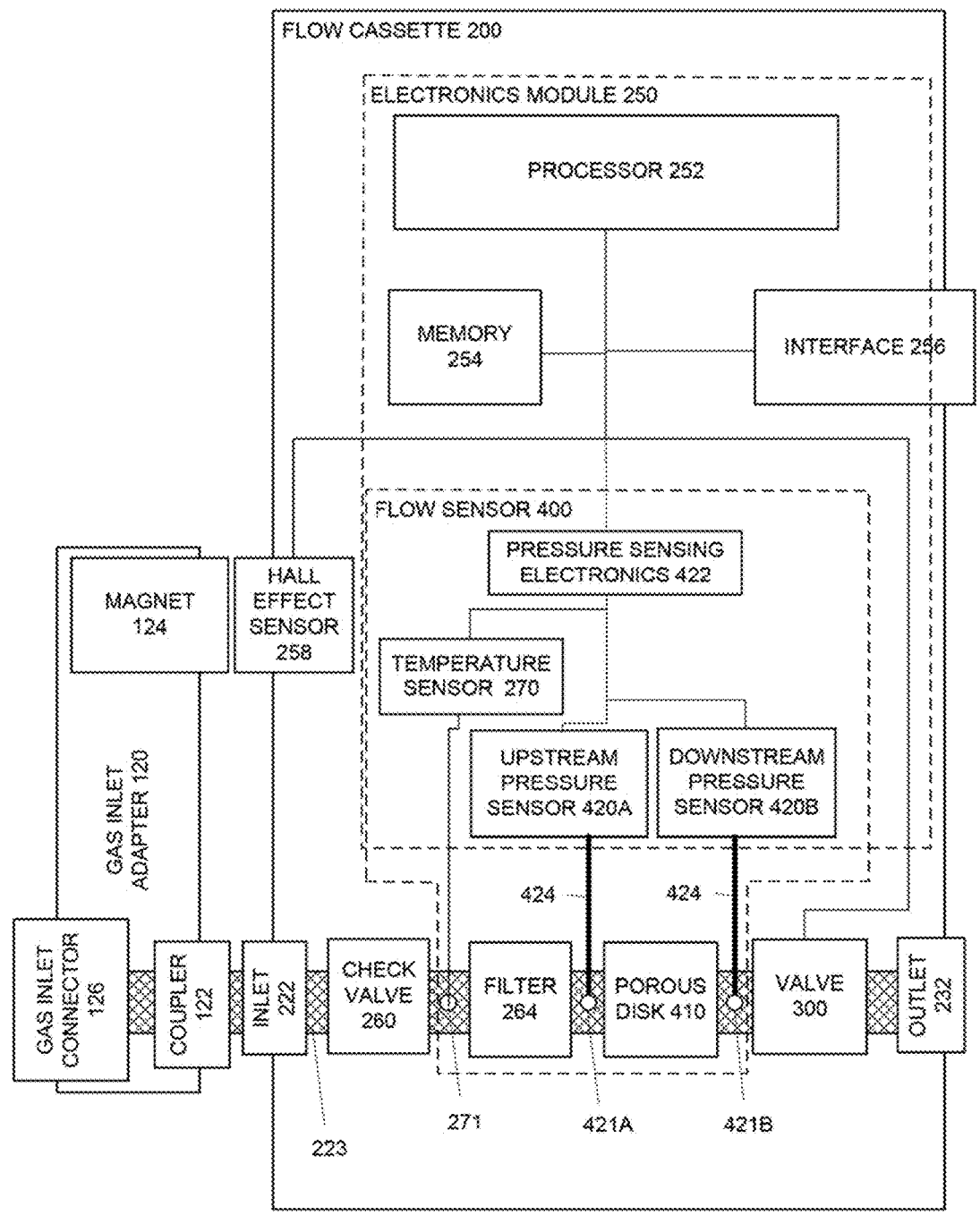
FIG. 3 is a block diagram of an exemplary flow sensor according to certain aspects of the present disclosure.

FIG. 3 is a block diagram of an exemplary flow cassette 200 according to certain aspects of the present disclosure. The flow cassette 200 includes an inlet 222 that is configured to sealingly mate with an input flow channel, for example a coupler 122 of the gas inlet adapter 120. The gas inlet adapter 120 also has an inlet connector (not shown in FIG. 3) that is fluidly connected to the coupler 122. Various breathing gases and gas mixtures are associated with individually unique connector types, sizes, and configurations, wherein the association is generally recognized in the medical industry. Each gas inlet adapter 120 has one or more inlet connectors that are adapted to respectively accept a connector that is unique to a certain type of gas or gas mixture. The number and placement of magnets 124 are uniquely associated with the inlet connector that will be coupled to the inlet of the flow cassette 200 when that gas inlet adapter 120 is installed in a ventilator and thereby mated with the flow cassette 200. In certain embodiments, the gas inlet adapter 120 may be configured to accept one or more of a standard composition of ambient air, a pure oxygen, and a heliox gas mixture.

The inlet 222 is fluidly connected to a passage 223 that runs through the flow cassette 200 to an outlet 232 that is configured to sealingly mate with an output flow channel of the ventilator 100 that, for example, leads to the supply limb 104. In this example embodiment, there are several elements disposed along the passage 223, including a check valve 260, a filter 264, a porous disk 410 and a valve 300. In certain embodiments, some of these elements may be omitted or arranged in a different order along the passage 223. In this embodiment, the flow cassette 200 also includes a Hall effect sensor 258 configured to detect the number and placement of the magnets 124 of the gas inlet adapter 120. By comparing the detected number and placement of the magnets 124 to stored information associating the number and placement of the magnets 124 with gases that will be accepted by the inlet connector that is coupled to the inlet of the flow cassette 200, the processor 252 can automatically determine what gas will be provided through the gas inlet adapter 120 as installed in the ventilator 100. In other embodiments, the gas inlet adapter 120 may include another type of indicator, for example a machine-readable element, that is associated with the configuration of the gas inlet adapter 120 and the flow cassette 200 may include a sensor that is capable of reading the machine-readable element and thereby automatically detecting the configuration of the gas inlet adapter 120.

The flow cassette 200 includes a flow sensor 400 that has a flow restriction 410 that, in this example, is a porous disk disposed in passage 223 such that all gas flowing through the passage 223 must pass through the porous disk 410. The flow sensor 400 also includes an upstream pressure sensor 420A and downstream pressure sensor 420B with gas passages 424 from the sensors to sensing ports 421A and 421B disposed in the passage 223 on upstream and downstream sides, respectively, of the porous disk 410. There is also a temperature sensor 270 that has a temperature sensing element 271 disposed in the passage 223. In conjunction with the knowledge of which gas is flowing through the porous disk 410, derived from the configuration of the gas inlet adapter 120 as indicated by the magnet 128 and sensed by the Hall effect sensor 258, and the knowledge of the temperature of the gas, as measured by the temperature sensor 270, the pressure drop can be used to determine the true flow rate, sometimes referred to as "the compensated flow rate," of the gas that is passing through the porous disk 410.

The pressure drop across the porous disk 410 is related in a monotonic way to the rate of gas passing through the porous disk 410. The porous disk 410 is characterized as to its flow resistance characteristics with a selection of gases and gas mixtures at a standard temperature. Without being bound by theory, certain gases, such as helium, have a smaller molecular size and pass more easily through the thickness of the porous disk 410 compared to a gas, such as nitrogen, with a larger molecule. Thus, a certain pressure drop will indicate a first flow rate for a small-molecule gas and a second, lower flow rate for a large-molecule gas. Gas mixtures will tend to have flow rates that reflect the percentage composition of the gases that make up the gas mixture. In certain embodiments, the pressure drops of certain predetermined medical gases and gas mixtures are specifically characterized for the porous disk 410 and stored in a look-up table contained in the memory 254 of the electronics module 250. The temperature of a gas also affects the pressure drop for a given flow rate of that gas flowing through the porous disk 410. In certain embodiments, the effect of the gas temperature is also characterized for the porous disk 410 and stored in the memory 254. In certain embodiments, the characterization of the flow characteristics of the porous disk 410, also referred to herein as "compensation parameters," are combined for gas type and temperature in a single look-up table. Those of skill in the art will recognize that such compensation parameters may be stored in other forms, for example equations that include scaling parameters, to enable conversion of a raw pressure drop measurement into an accurate flow rate.

The flow cassette 200 includes an electronics module 250. In certain embodiments, the conversion of the raw pressure measurements by pressure sensors 420A, 420B into a pressure drop measurement is accomplished in a separate pressure sensing electronics 422 and provided to a flow sensor processor 252. In certain embodiments, the pressure sensing electronics 422 may provide the processor 252 with individual pressure signals for pressures that are upstream and downstream of the porous disk 410. In certain embodiments, there may also be a front connection panel 160 for connection to, for example, external instruments, sensors, or sensor modules. In certain embodiments, the pressure sensors 420A, 420B may provide the raw signals directly to the processor 252. In certain embodiments, the pressure sensors 420A, 420B may include conversion circuitry such that each sensor 420A, 420B provides a pressure signal directly to the processor 252.

In certain embodiments, the temperature sensor 270 provides a signal that includes a temperature to the pressure sensing electronics 422. In certain embodiments, the temperature sensor 270 provides this temperature signal directly to the processor 252. In certain embodiments, the temperature sensing element 271 may be connected directly to the pressure sensing electronics 422 or to the processor 252. In certain embodiments, the temperature sensor 270 may be configured to sense the gas temperature over a range of temperatures of at least 5-50° C. In certain embodiments, the temperature sensor 270 may be configured to sense the gas temperature over a range of temperatures of at least 5-50° C.

The processor 252 is connected to the memory 254 and an interface module 256 as well as the sensors 270, 420A, and 420B. The various drive, sensing, and processing functions of these sensors 270, 420A, and 420B may be accomplished in various different modules, such as the processor 252 and pressure sensing electronics 422, depending on the particular design and layout of the flow cassette 250 without departing from the scope of this disclosure. For example, a processor 252 may be configured to provide a supply an electrical current directly to the temperature sensing element 271 and to directly measure a voltage drop across the temperature sensing element 271 without the need for intervening electronics. All functions disclosed herein may be accomplished in the block elements of FIG. 3 as described or in alternate blocks and the blocks depicted in FIG. 3 may be combined or divided without departing from the scope of this disclosure.

The memory 254 is configured to store operating instructions for the processor 252 and data that may include calibration data for the sensors 258, 270, 420A, and 420B. The data may also include information, as discussed above, such as equations or look-up tables to use the two pressure measurements from pressure sensors 420A and 420B and the temperature measurement from the temperature sensor 270 to determine a flow rate through the porous disk 410. In certain embodiments, the memory comprises non-volatile memory such as magnetic disk, a solid-state memory, a flash memory, or other non-transient, non-volatile storage device as known to those of skill in the art.

The processor 252 is also operatively coupled to the valve 300 and is capable of actuating the valve 300. The interconnection of the processor 252 with the other elements as shown in FIG. 3 may be accomplished by direct connection via any technology known to those of skill in the art, for example twisted-pair wires or fiber-optic cables, or via a network connection with microprocessors embedded in the other elements. The interface module 256 may include signal transceivers for wired or wireless communication with other devices within the ventilator 100 or may connector to an external interface, such as the rear interface panel 165 shown in FIG. 2B, to communicate with devices external to the ventilator 100.

Figure 4A:
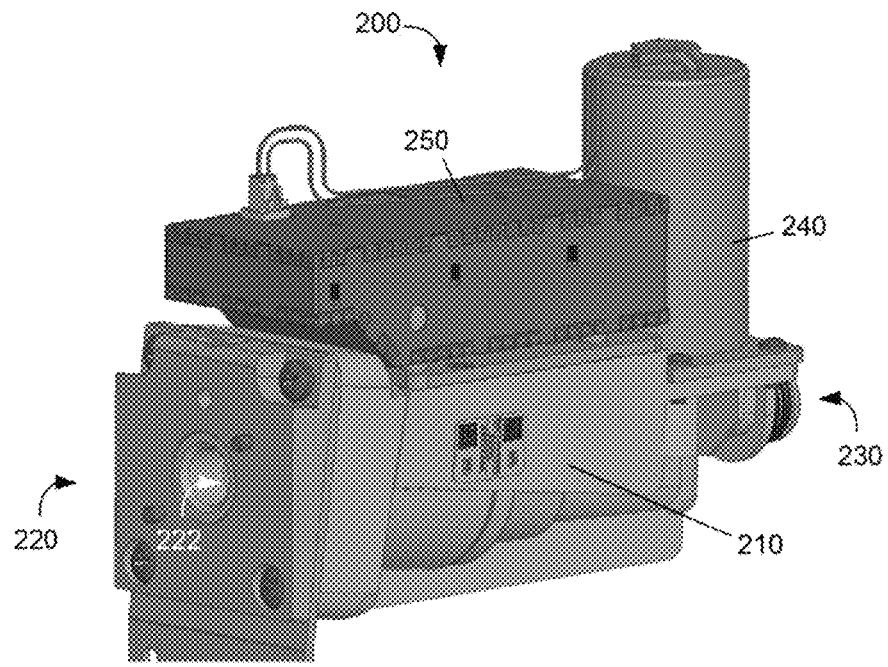
FIG. 4A depicts an exemplary flow cassette according to certain aspects of the present disclosure.

FIG. 4A depicts an exemplary flow cassette 200 according to certain aspects of the present disclosure. The flow cassette 200 has a body 210 with an inlet end 220 and an outlet end 230. At the inlet end 220, there is the inlet 222 that is configured to sealingly mate with a coupler 122 (not shown in FIG. 4A) of a gas inlet adapter 120. The inlet end 220 may also include locating features 226, for example protruding pins, that align the gas inlet adapter 120 to the inlet 222 and a mating face 224 that provides a reference surface for the mated gas inlet adapter 120. A solenoid 240 is attached to the body proximate to the outlet end 230 to drive a pressure control valve (not visible in FIG. 4A) disposed within the body 210. The electronics module 250 is attached, in this embodiment, to the top of the body 210. The details of the electronics module are discussed in greater detail with respect to FIG. 3.

Figure 4B:
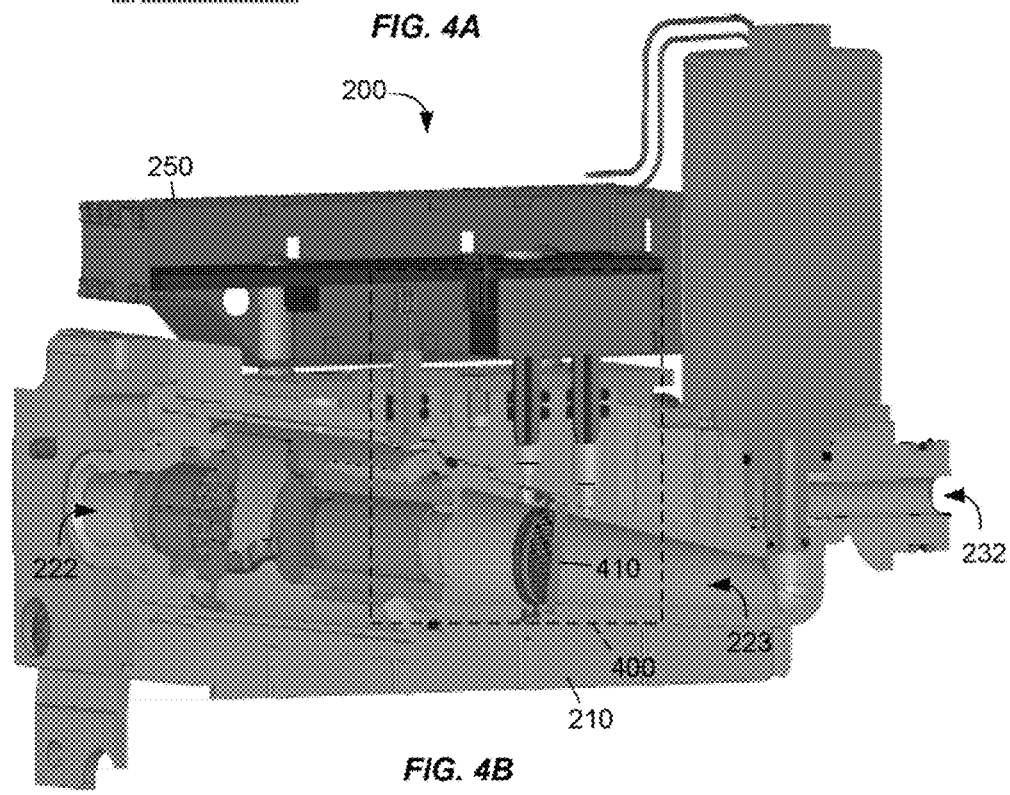
FIG. 4B is a cross-section of the flow cassette of FIG. 4A according to certain aspects of the present disclosure.

FIG. 4B is a cross-section of the flow cassette of FIG. 4A according to certain aspects of the present disclosure. The dashed-line box 400 indicates the elements that make up the flow sensor 400, which is discussed in greater detail with respect to FIGS. 3 and 4C. The passage 223 that connects the inlet 222 and outlet 232 is visible in the cross-section of FIG. 4B, with the porous disk 410 disposed within the passage 223.

Figure 4C:
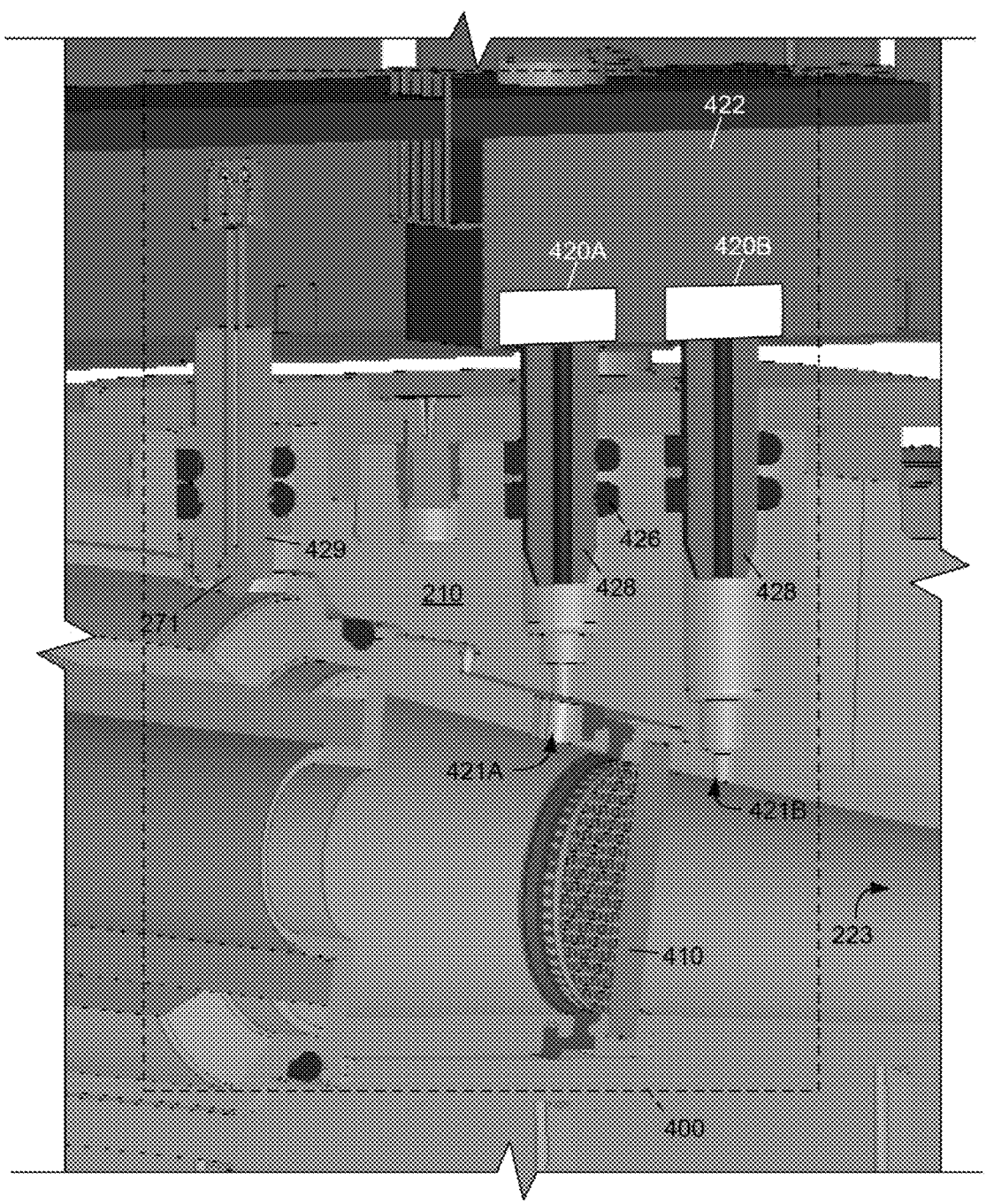
FIG. 4C is an enlarged view of a portion of FIG. 4B showing an exemplary flow sensor according to certain aspects of the present disclosure.

FIG. 4C is an enlarged view of a portion of FIG. 4B showing the exemplary flow sensor 400 according to certain aspects of the present disclosure. In this example, the pressure sensors 420A, 420B are disposed within the package of the pressure sensing electronics 422 and connected to the passage 223 by gas passages 424 leading to sensing ports 421A and 421B. The temperature sensing element 271 is exposed to the interior of the passage 223 and therefore in contact with the gas within the passage 223. Seals 426, in this example a pair of o-rings, provide a gas-tight seal between the housing 210 and the tube extensions 428 for the gas passages 424 and a feed-through 429 for the temperature sensing element 271.

Figure 5:
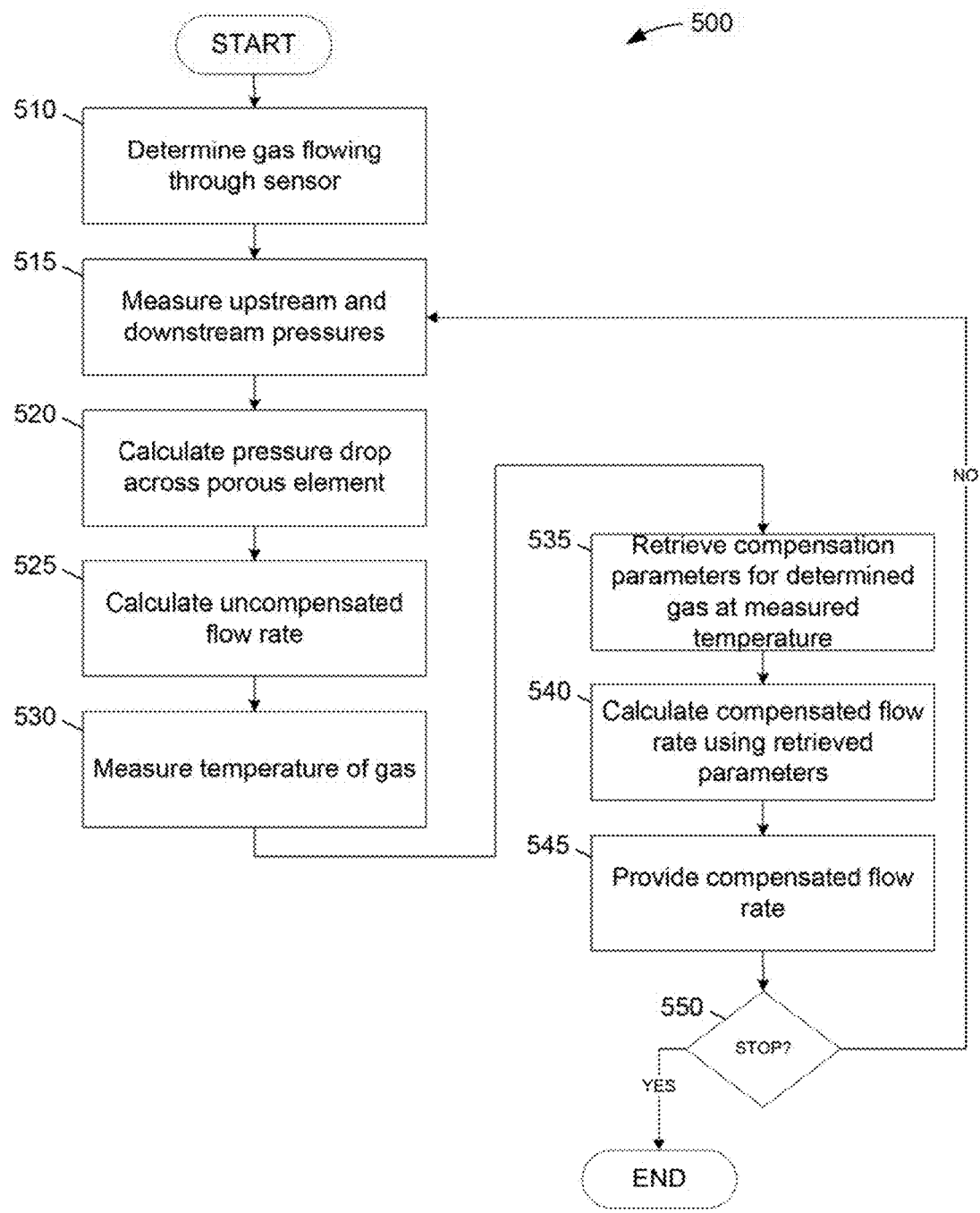
FIG. 5 is a flow chart of an exemplary flow measurement process according to certain aspects of the present disclosure.

FIG. 5 is a flow chart of an exemplary flow measurement process 500 according to certain aspects of the present disclosure. The process 500 starts in step 510 by determining which gas or gas mixture, for example oxygen or heliox 70/30, will be flowing through the flow sensor 400. In step 515, the gas pressures upstream and downstream of the flow restriction 410 are measured and a pressure drop across the flow restriction 410 is calculated in step 520. In step 525, the processor 252 calculates an uncompensated flow rate based at least partially on the pressure drop. The temperature of the gas flowing through the flow sensor 400 is measured in step 530 and in step 535 the processor 252 loads information from the memory 254 that may include compensation parameters related to the flow sensor 400. The processor 252 calculates a compensated flow rate using the retrieved compensation parameters in step 540 and provides this compensated flow rate, for example to a processor of the ventilator 100, in step 545. Step 550 is a decision point that checks whether a "stop" command has been received, in which case the process 500 branches along the "yes" path to the end and terminates. If a "stop" command has not been received, the process 500 branches along the "no" path back to step 515 and measures the pressures and temperature. The process 500 will loop through the steps 515-550 until a "stop" command is received.

In summary, it can be seen that the disclosed embodiments of the flow sensor provide an accurate measurement of a gas flow rate in a compact and modular form. The accuracy of the flow rate may be improved by compensating for one or more of the gas temperature and the gas composition. This compensation may be accomplished through prior experimental calibration of the particular flow restriction, e.g. porous disk, or calculations based on gas flow theory. The modular form enables this subsystem to be independently tested and calibrated as well as simplifying assembly and replacement.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

To the extent that the terms "include," "have," or the like are used in the description or the claims, such terms are intended to be inclusive in a manner similar to the term "comprise" as "comprise" is interpreted when employed as a transitional word in a claim.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A flow sensor comprising:
   a flow restriction disposed within a passage such that a fluid passing through the passage must pass through the flow restriction;

an upstream pressure sensor coupled to the passage at a point upstream of the flow restriction and configured to measure and provide an upstream pressure of the fluid within the passage;

a downstream pressure sensor coupled to the passage at a point downstream of the flow restriction and configured to measure and provide a downstream pressure of the fluid within the passage;

pressure sensor electronics coupled to the upstream pressure sensor and the downstream pressure sensor and configured to determine a pressure drop measurement;

a filter coupled to the passage upstream of the upstream pressure sensor;

a temperature sensor coupled to the passage upstream of the filter and configured to measure and provide a temperature of the fluid within the passage;

a package for housing the upstream pressure sensor, the downstream pressure sensor, the pressure sensor electronics, and the temperature sensor, wherein the upstream pressure sensor is connected to the passage through a first gas passage, the downstream pressure sensor is connected to the passage through a second gas passage, and the temperature sensor is connected to the passage through a feed-through connected to the passage upstream of the filter;

a non-volatile memory configured to store compensation parameters which characterize flow resistance characteristics of the flow restriction, the compensation parameters comprising a pressure drop of at least one predetermined fluid characterized for the flow restriction; and a flow sensor processor coupled to the memory, the upstream and downstream pressure sensors and the temperature sensor and configured to accept measurements therefrom and calculate a compensated flow rate based at least in part on the measured pressures and temperature.

2. The flow sensor of claim 1, wherein:
the non-volatile memory is configured to store executable instructions;
the flow sensor processor is configured by retrieving the executable instructions from the memory to further retrieve the compensation parameters from the memory; and
the calculation of the compensated flow rate is based at least in part on the retrieved compensation parameters.

3. The flow sensor of claim 2, wherein:
the flow sensor processor is further configured to accept an identification of the fluid that is passing through the passage;
the compensation parameters comprise characteristics of the flow restriction that are related to a plurality of predetermined fluids;
the retrieved compensation parameters comprise characteristics of the flow restriction related to the identified fluid; and
the calculation of the compensated flow rate is based at least in part on the retrieved compensation parameters that are related to the identified fluid.

4. The flow sensor of claim 3, wherein the characteristics of the flow restriction are predetermined for each of the plurality of predetermined fluids.

5. The flow sensor of claim 4, wherein the plurality of predetermined fluids comprises one or more medical gases.

6. The flow sensor of claim 5, wherein the plurality of predetermined fluids comprises one or more of a standard composition of ambient air, a pure oxygen, and a heliox gas mixture.

7. The flow sensor of claim 4, wherein the characteristics of the flow restriction are predetermined for each of the plurality of predetermined fluids over a range of temperatures.

8. The flow sensor of claim 7, wherein the range of temperatures comprises at least 5-50° C.

9. The flow sensor of claim 1, wherein the flow restriction comprises a porous disk.

10. The flow sensor of claim 1, further comprising a temperature sensing element connected to the temperature sensor through the feed-through.

11. A ventilator comprising:
a sensor configured to detect a number and placement of at least one magnet of a gas inlet adapter, the number and placement of the one or more magnets associated with a gas;
an output flow channel configured to mate with a supply limb;
an input flow channel configured to accept the gas from a source; and
a flow sensor comprising:
a flow restriction disposed within a passage coupled between the input flow channel and the output flow channel such that the gas passing through the passage must pass through the flow restriction;
an upstream pressure sensor coupled to the passage at a point upstream of the flow restriction and configured to measure and provide an upstream pressure of the gas within the passage;
a downstream pressure sensor coupled to the passage at a point downstream of the flow restriction and configured to measure and provide an downstream pressure of the gas within the passage;
pressure sensor electronics coupled to the upstream pressure sensor and the downstream pressure sensor and configured to determine a pressure drop measurement;
a filter coupled to the passage upstream of the upstream pressure sensor;
a temperature sensor coupled to the passage upstream of the filter and configured to measure and provide a temperature of the gas within the passage;
a non-volatile memory configured to store compensation parameters which characterize flow resistance characteristics of the flow restriction, the compensation parameters comprising a pressure drop of at least one predetermined fluid characterized for the flow restriction;
a flow sensor processor coupled to the memory, the upstream and downstream pressure sensors and the temperature sensor and configured to accept measurements therefrom and calculate a compensated flow rate based at least in part on the measured pressures and temperature; and
a package for housing the upstream pressure sensor, the downstream pressure sensor, and the pressure sensor electronics, the temperature sensor, and the flow sensor processor, wherein the upstream pressure sensor is connected to the passage through a first gas passage, the downstream pressure sensor is connected to the passage through a second gas passage, and the temperature sensor is connected to the passage through a feed-through connected to the passage upstream of the filter.

12. The ventilator of claim 11, wherein:

the non-volatile memory is configured to store executable instructions;

the flow sensor processor is configured by retrieving the executable instructions from the memory to further retrieve the compensation parameters from the memory; and the calculation of the compensated flow rate is based at least in part on the retrieved compensation parameters.

13. The ventilator of claim 12, further comprising:

the gas inlet adapter having the at least one magnet associated with the gas being supplied to the input flow channel; and a central processor coupled to the sensor and the flow sensor processor, the central processor configured to identify the gas that will be passing through the flow sensor from the detected orientation of the gas inlet adapter, wherein:

the flow sensor processor is further configured to accept an identification of the gas that is passing through the flow sensor, the identification based on the number and placement of the at least one magnet of the gas inlet adapter;

the compensation parameters comprise characteristics of the flow restriction that are related to a plurality of predetermined gases;

the retrieved compensation parameters comprise characteristics of the flow restriction related to the identified gas; and the calculation of the compensated flow rate is based at least in part on the retrieved compensation parameters that are related to the identified gas.

14. The ventilator of claim 13, wherein the characteristics of the flow restriction are predetermined for each of the plurality of predetermined gases.

15. The ventilator of claim 14, wherein the plurality of predetermined gases comprises one or more medical gases.

16. The ventilator of claim 15, wherein the plurality of predetermined gases comprises one or more of a standard composition of ambient air, a pure oxygen, and a heliox gas mixture.

17. The ventilator of claim 14, wherein the characteristics of the flow restriction are predetermined for each of the plurality of predetermined gases over a range of temperatures.

18. The ventilator of claim 17, wherein the range of temperatures comprises at least 5-50° C.

19. The ventilator of claim 11, wherein the flow restriction comprises a porous disk.

20. The ventilator of claim 11, further comprising a temperature sensing element connected to the temperature sensor through the feed-through.

* * * * *